US00PP16748P3

(12) United States Plant Patent

Sandler-Ziv et al.

(10) Patent No.: US PP16,748 P3

(45) Date of Patent: Jul. 4, 2006

(54) *NARCISSUS* PLANT NAMED 'INBAL'

(50) Latin Name: *Narcissus tazetta*
Varietal Denomination: Inbal

(75) Inventors: Dorit Sandler-Ziv, Nes Ziona (IL); Herut Yahel, Rishon LeZion (IL); Avner Cohen, Nes Ziona (IL); Har'el Yon, Rehovot (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 10/886,031

(22) Filed: Jul. 8, 2004

(65) Prior Publication Data

US 2006/0010544 P1 Jan. 12, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

Postproduction Longevity of Flowering Potted Bulbs Nell et al. 1996.*

* cited by examiner

*Primary Examiner*—Anne Marie Grunberg
*Assistant Examiner*—Annette H Para
(74) *Attorney, Agent, or Firm*—Foley & Lardner LLP

(57) ABSTRACT

A new and distinct *Narcissus* plant named 'Inbal' particularly characterized by 10 to 15 flowers per stem; white flower; flower diameter 54–57 mm; length of outer perianth segment: 24–27 mm; width of outer perianth segment 21–23; and having mild fragrance.

2 Drawing Sheets

Latin name of the genus and species of the claimed plant: *Narcissus tazetta.*
Variety denomination: Inbal.

BACKGROUND OF THE INVENTION

The present invention relates to a new and distinct cultivar of a *Narcissus* plant, botanically known as *Narcissus tazetta* L., 'Paperwhite' group, commonly known as daffodil and hereinafter referred to by the cultivar name 'Inbal'.

The new cultivar originated from a cross made in a controlled breeding program in Bet Dagan, Israel. The female parent is a *Narcissus* variety from a proprietary breeding line designated '1959/4' (unpatented). The male parent is a *Narcissus* variety from a proprietary breeding line designated '66/18/7' (unpatented).

'Inbal' was discovered and selected by the inventors Dorit Sandler-Ziv, Herut Yahel, Avner Cohen and Har'el Yon, as a flowering plant within the progeny of the stated cross in a controlled environment in Bet Dagan, Israel.

Asexual propagation of the new cultivar by either separation of bulblets, bulb chips (twin scaling), or bulb crossing (scoring) was first performed in 1995 in Bet Dagan, Israel and has demonstrated that the combination of characteristics as herein disclosed for the new cultivar are firmly fixed and retained through successive generations of asexual propagation. The new cultivar reproduces true-to-type.

BRIEF SUMMARY OF THE INVENTION

The following traits have been repeatedly observed and are determined to be basic characteristics of 'Inbal' which in combination distinguish this *Narcissus* as a new and distinct cultivar:

1. 10 to 15 flowers per stem;
2. white flower;
3. flower diameter 35–40 mm;
4. length of outer perianth segment: 17–19 mm;
5. width of outer perianth segment: 18–22 mm, and
6. mild fragrance.

'Inbal' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown Bet Dagan, Israel under conditions which closely approximate those generally used in commercial practice.

Plants of the new *Narcissus* cultivar 'Inbal' differ from plants of the female parental cultivar, '1959/4' (unpatented) in the following characteristics: 1) 'Inbal' has a stronger stem than '1959/4'; 2) 'Inbal' has better overlapping of sepals than '1959/4'; and 3) the fragrance of the flower of 'Inbal' is not as strong as '1959/4'. Plants of the new *Narcissus* cultivar 'Inbal' differ from plants of the male parental cultivar, '66/18/7' (unpatented) in the following characteristics: 1) the flower size of 'Inbal' is smaller than '66/18/7 '; 2) the strength of the flower of 'Inbal' is stronger than '66/18/7'; and 3) the fragrance of the flower of 'Inbal' is not as strong as '66/18/7'.

Of the many commercial cultivars known to the present inventors, the most similar in comparison to 'Inbal' is cultivar 'Ziva' (U.S. Plant Pat. No. 3,366). The following table is a comparison between the new variety 'Inbal' and 'Ziva', as grown under the same conditions:

TABLE 1

| Characteristic | 'Inbal' | 'Ziva' |
|---|---|---|
| Plant height | About 35 cm | About 60 cm |
| Diameter of flower | 35–40 mm | About 45 mm |
| Fragrance | Mild | Strong |
| Anthers of outer whorl: Position as compared to the mouth of the perianth tube | Beneath | Above |
| Anthers of inner whorl: Position as compared to the mouth of the perianth tube | Beneath | Same level |

BRIEF DESCRIPTION OF THE DRAWING

The accompanying photographic drawings illustrate the overall appearance of the new *Narcissus* showing the colors as true as is reasonably possible with colored reproductions of this type.

The first photograph shows an 'Inbal' plant in its entirety as a potted plant with several inflorescences, 2 months after planting of the bulb.

The second photograph shows a close-up of an 'Inbal' inflorescence, 2 months after planting of the bulb.

DETAILED BOTANICAL DESCRIPTION

Natural growing conditions of the new *Narcissus* in Israel in a typical Mediterranean climate are as follows:

Planting: End of September through beginning of November in medium to heavy soil, pH 6–8. Planting material: bulb offsets, 8–12 cm in circumference size.
Growing: 5–6 months in winter in night temperatures of 0–10° C., and daytime temperatures of 8–20° C.
Flowering: 45–60 days after planting from mid-December through mid-January.
Bulb flowering size: >10 cm.
Bulb filling and maturation: 2–3 months (mid-March to end of May) in night temperatures of 8–16° C., and daytime temperatures of 16–30° C.
Bulb harvest: In June, after leaf yellowing.
Bulb curing: 2–3 weeks in well-aired shed at 20–35° C.
Bulb sorting and strorage: Round bulbs >12 cm. (marketing size for cut flower and pot-plant production).
Shipping and storage: 25–30° C., 60% humidity, for 2–6 months, under well-aired conditions.

Offsets <12 cm=propagation material, storage: aired shed.

Forcing: For cut flower and pot-plant production: Pre-treatment of bulbs: bulbs stored in 25–30° C. should be transferred to 9–13° C. for 3–4 weeks prior to planting.
Planting: In well-drained, pH 6–7 sterilized planting medium.
Growing temperatures: Night: 13–17° C., day: 17–23° C.
Flowering: 25–40 days after planting (temperature dependent).
Propagation:
*Method.*—Star cutting or cross-cutting bulbs of size >16 cm from mid-July through mid-August.
*Storage.*—Aired shed, 25–30° C.
*Planting.*—In October.
*Harvest.*—June, at the end of the growing season, bulb size 6–12 are harvested for use as propagation material.

The following observations, measurements and values describe the new cultivar as grown in Bet Dagan, Israel under conditions which closely approximate those generally used in commercial practice. Color references are made to The Royal Horticultural Society Colour Chart (R.H.S.), except where general colors of ordinary significance are used. Color values were taken under daylight conditions at mid-February in Bet Dagan, Israel. The age of the plant described is about 50 days after planting in mid-December of bulbs with 10 cm circumference.

Parentage:
*Male parent.*—66/18/7 (own breeding line).
*Female parent.*—1959/4 (own breeding line).
Propagation: Vegetative propagation from bulbs by separation of bulblets, bulb chips (twin scaling), or bulb crossing (scoring).
Plant:
*General appearance and form.*—Height: Approximately 35 cm. Spread: About 25 cm. Growth habit: Semi-erect. Growth rate: Fast. Position of inflorescence in relation to foliage: Above. Flowering response: Dependent upon cold and heat treatment of bulb. Flowering season: End of winter. Winter hardiness/weather tolerance: Very good. Lastingness of the Individual bloom: About one week.
*Rooting habit.*—Many fleshy roots sprouting from the disc at the base of the bulb.
Scape:
*Length.*—About 30 cm.
*Diameter.*—6–9 mm.
*Shape in cross section at ground level.*—Elliptic.
*Shape in cross section of upper third.*—Narrow elliptic. Ribbing: Medium pronounced.
Foliage:
*Arrangement.*—Rosette, exerting from bulb.
*Overall shape.*—Linear.
*Apex.*—Acute.
*Length.*—40–45 cm.
*Width.*—20–30 mm.
*Margin.*—Entire.
Texture: Smooth.
*Surface.*—Glabrous.
*Color of upper surface.*—Mature leaf: Green RHS 137 C. Immature leaf: Green RHS 137 C.
*Color of lower surface.*—Mature leaf: Dark green RHS 137 B. Immature leaf: Dark green RHS 137 B.
*Venation.*—Inconspicuous (both upper and lower surfaces).
Bud:
*Length.*—About 10 mm.
*Diameter.*—About 5 mm.
*Color of bract before opening.*—Green.
Umbel:
*Height.*—Approximately 10 cm.
*Diameter.*—Approximately 10 cm.
Bulb:
*Shape.*—Short-necked basically rounded, somewhat edged resulting from splitting.
*Size.*—Variable with age.
*Color of outer scale.*—Dark brown.
Flower:
*Type.*—Single.
*Shape.*—Actinomorphic.
*Diameter of perianth.*—35–40 mm.

*Number of perianth segments.*—Three inner and three outer segments.
*Attitude of perianth relative to floral axis.*—Incurved.
*Position of segments.*—Overlapping.
*Length of outer perianth segment.*—17–19 mm.
*Width of outer perianth segment.*—18–22 mm.
*Shape in cross section of perianth segment.*—Incurved.
*Shape of tip of perianth segment.*—Mucronate.
*Margin of perianth segment.*—Entire.
*Surface of perianth segment.*—Smooth, midrib raised.
*Length of perianth tube.*—18–20 mm.
*Color of upper surface of perianth.*—White RHS 155 D. Color of lower surface of perianth: White RHS 155 D.
*Fragrance.*—Mild.

Corona:
*Height.*—6 mm.
*Diameter of top.*—9–10 mm.
*Color of outer side.*—White RHS 155 D.
*Color of inner side.*—White RHS 155 D.
*Margin.—E ntire.*
*Reflexing of margin.*—Absent.
*Lobing.*—Absent.

Pedicel:
*Length.*—48–56 mm.
*Diameter.*—About 2 mm.

Anthers:
*Anthers of outer whorl.*—Position as compared to the mouth of the perianth tube: Beneath.
*Anthers of inner whorl.*—Position as compared to the mouth of the perianth tube: Beneath.
*Color of anther.*—Yellowish.
*Curling of anther.*—Absent.
*Color of pollen.*—Yellow.

Style:
*Color.*—White.

Stigma:
*Position as compared to anthers of outer whorl.*—Beneath.
*Position as compared to anthers of inner whorl.*—Above.
*Color.*—White.

Ovary:
*Shape.*—Triangular, ribbed.

Fruit:
*Shape.*—Triangular.
*Color.*—Medium green RHS 137 C.
*Length.*—About 8–9 mm.
*Diameter.*—6–7 mm.

Seed:
*Length.*—2–3 mm.
*Shape.*—Ribbed.
*Color.*—Black.

Disease/pest resistance: Highly resistant to *Fusarium oxysporum*. Other diseases have not been observed not tested for.

Disease/pest susceptibility: Not tested; no information currently available.

We claim:

1. A new and distinct *Narcissus* plant named ‘Inbal’, as illustrated and described herein.

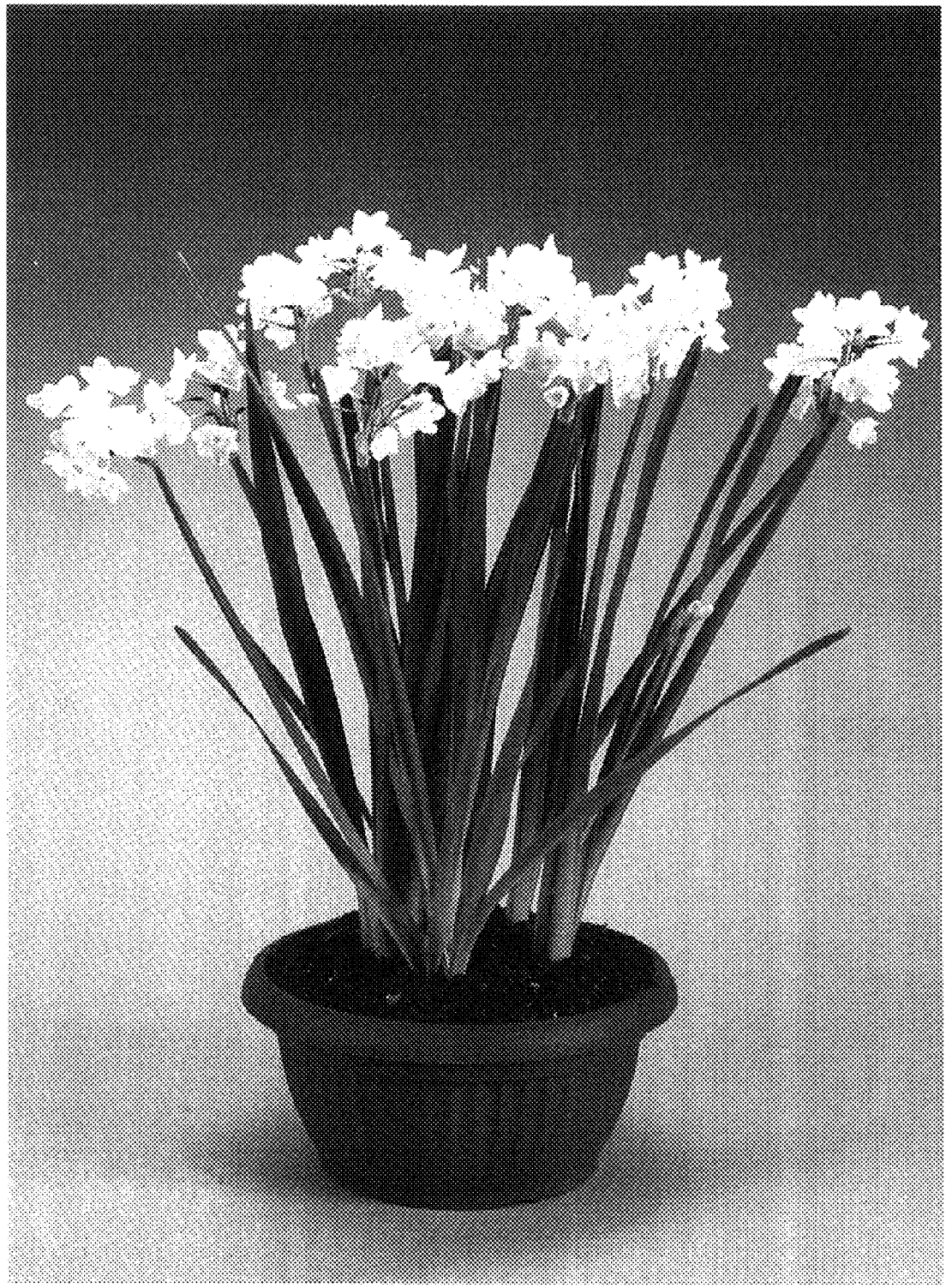

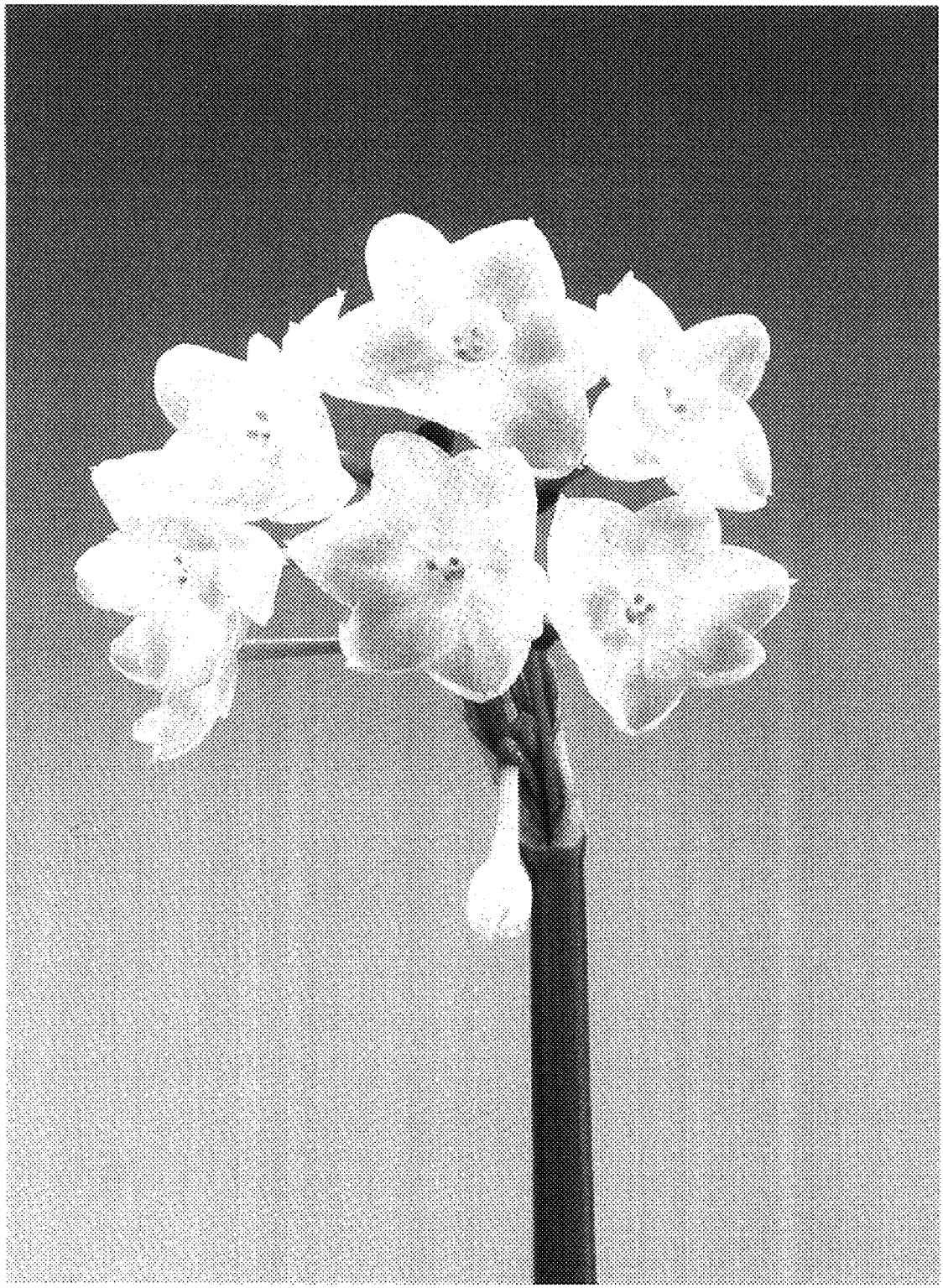

* * * * *